United States Patent [19]

Shigeyasu et al.

[11] 3,959,449

[45] May 25, 1976

[54] METHOD OF RECOVERING HEAVY METAL [-BROMINE] BROMIDES AND HYDROBROMIC ACID CATALYSTS FOR LIQUID-PHASE OXIDATION [CATALYST]

[75] Inventors: Motoo Shigeyasu; Takeo Ozaki; Nobuo Kusano, all of Matsuyama, Japan

[73] Assignee: Matsuyama Petrochemicals Inc., Osaka, Japan

[22] Filed: Apr. 1, 1974

[21] Appl. No.: 456,717

[30] Foreign Application Priority Data
Mar. 30, 1973 Japan.............................. 48-36351
Apr. 26, 1973 Japan.............................. 48-47826

[52] U.S. Cl.................................. 423/488; 423/1; 423/481; 423/491; 423/493; 423/658.5
[51] Int. Cl.² .................... C01B 7/12; C01G 51/08; C01G 45/06; B01D 11/02
[58] Field of Search ........... 423/488, 492, 493, 481, 423/491, 658.5, 1

[56] References Cited
UNITED STATES PATENTS
3,686,076   8/1972   Cuppler et al.................. 423/488 X OTHER PUBLICATIONS
Book, "Ion Exchange Resins," by Robert Kunin, 1978 Ed., p. 204, John Wiley & Sons, Inc., New York.

Primary Examiner—Edward Stern
Attorney, Agent, or Firm—Sughrue, Rothwell, Mion, Zinn & Macpeak

[57] ABSTRACT

A method of recovering in highly pure states heavy metals such as cobalt, manganese, etc., and bromine without the contamination of organic impurities and heavy metal impurities from the residue of the reaction mother liquor, which is obtained by removing a solvent from the reaction mother liquor remained after recovering terephthalic acid from the oxidation reaction product obtained in the method of producing terephthalic acid by subjecting an alkylbenzene such as p-xylene to a liquid phase oxidation with oxygen or oxygen-containing gas in the presence of a catalyst containing the heavy metals and bromine using a lower aliphatic monocarboxylic acid as the solvent, said method comprising: stirring the residue of the reaction mother liquor with water as solvent in the presence of molecular oxygen and a sulfur compound, removing solid impurities from the extracted mixtures thus treated by solid-liquid separation to provide an aqueous catalyst extract solution, passing the aqueous solution through a column packed with a strongly acidic cation-exchange resin to adsorb thereon the heavy metal catalyst, distilling the solution thus passed through the ion-exchange resin to recover bromine contained in the aqueous extract solution as hydrobromic acid, and, on the other hand, passing hydrobromic acid through the column of the ion exchange resin having adsorbed thereon the heavy metal catalyst to desorb the heavy metal catalyst, whereby the heavy metal catalyst is recovered as the bromide of it.

20 Claims, 2 Drawing Figures

METHOD OF RECOVERING HEAVY METAL [-BROMINE] BROMIDES AND HYDROBROMIC ACID CATALYSTS FOR LIQUID-PHASE OXIDATION [CATALYST]

BACKGROUND OF THE INVENTION

1. Field of the Invention

The present invention relates to a method of recovering from the reaction mother liquor residue the oxidation catalyst used for producing terephthalic acid by liquid-phase oxidation of an alkylbenzene such as p-xylene with a molecular oxygen-containing gas. More particularly, the invention relates to a method of recovering heavy metals such as cobalt, manganese, etc., and bromine simultaneously in high pure states in the production of terephthalic acid by the liquid-phase oxidation of an alkylbenzene using an oxidation catalyst composed of the heavy metals and bromine.

2. Description of the Prior Art

Various methods have been proposed for producing terephthalic acid industrially and among them a method of producing terephthalic acid by liquid-phase oxidation of an alkylbenzene such as p-xylene with a molecular oxygen-containing gas in the presence of heavy metals such as cobalt, manganese, etc., and bromine as catalyst using a lower aliphatic monocarboxylic acid as solvent has been widely employed as SD process.

The desired material, terephthalic acid is separated from the reaction product of the liquid-phase oxidation of alkylbenzene by means of filtration, centrifugal separation, etc., and then the reaction solvent is recovered from the reaction mother liquor by means of distillation, etc. However, since the residue thus formed after recovering the solvent contains a large amount of the oxidation catalyst, it is necessary for utilizing effectively such an expensive heavy metal as cobalt and manganese and bromine to recover the catalyst for reuse.

The aforesaid reaction mother liquor residue contains, however, a large amount of organic impurities such as the unreacted alkylbenzene, such intermediates as 4-carboxybenzaldehyde, p-toluic acid etc., and by-products of the oxidation reaction having unknown structures besides the oxidation catalyst. Furthermore, in the liquid-phase oxidation as mentioned above, a monocarboxylic acid such as acetic acid is used as the reaction solvent and also bromine is used as one component of the oxidation catalyst under severe reaction conditions as high temperature and high pressure and hence the materials of the reaction apparatus are corroded as the reaction liquid retains in the reaction system and is circulated therein, which results in the contamination of the reaction liquid with metals of the corroded materials such as iron, lead, nickel, molybdenum, tungsten, copper, chromium, zinc, cadmium, etc. Still further, terephthalic acid produced by the oxidation reaction is gradually accumulated on the inside walls of such equipment and conduit owing to the sparing solubility thereof in the reaction solvent and clogging of conduits occurs. Thus the inside of the reaction system is washed with an aqueous solution of an alkali such as sodium hydroxide, which sometimes results in the contamination of the reaction liquid with the alkali metal.

It is known that those impurities impede the oxidation reaction of the alkylbenzene to cause the reduction of the quality and the yield of terephthalic acid. Therefore, it is important in using repeatedly the oxidation catalyst to recover the oxidation catalyst from the residue of the reaction mother liquor so that the organic impurities, heavy metal impurities, alkali metal, etc., as described above do not enter the catalyst recovered.

Various methods have already been proposed for recovering such an oxidation catalyst without being accompanied by the contamination of the various impurities as described above. For example, a method of recovering the oxidation catalyst is disclosed in U.S. Pat. No. 3,341,470 in which the residue of the reaction mother liquor of the liquid-phase oxidation reaction is incinerated to oxidize the heavy metal catalyst therein, the residue thus incinerated is dissolved in a mineral acid such as sulfuric acid, etc., a reducing agent such as sodium sulfide, hydrogen sulfide, etc., is added to the solution to remove copper contained in the residue as an impurity as the precipitate of copper sulfide, the solution is, then, diluted with water followed by addition of a hydroxide to adjust the pH thereof to about 4, calcium carbonate is added to the solution to precipitate such metal impurities as iron, chromium, etc. as oxides, sodium carbonate is added further to the solution from which the aforesaid metal impurities have been removed to precipitate heavy metals such as cobalt and manganese as the precipitate of the carbonate thereof, and finally the residual solution is treated with an organic carboxylic acid to recover the heavy metals as the salt of the organic carboxylic acid.

Also, according to other method as described in U.S. Pat. No. 2,964,559 the reaction mother liquor residue containing the by-product of the oxidation reaction is extracted with water to recover the oxidation catalyst as the extract and removing insoluble solid impurities, the aqueous extract containing the oxidation catalyst is adjusted to pH 4-5 with an alkali, whereby tarry by-products are removed as floats and also iron is removed as the precipitate of basic iron acetate, and further an alkali is added to the remaining aqueous solution, whereby the heavy metals such as cobalt and manganese are recovered as the precipitate of the carbonates.

Furthermore, according to still other method as described in Japanese Pat. Application Laid Open No. 34,088/'72 the reaction mother liquor residue containing the aforesaid impurities together with the oxidation catalyst is extracted with water to remove insoluble solid impurities, the pH of the aqueous extract thus obtained is adjusted to 6.0-6.8 by the addition of an alkali to remove iron and lead as the sparingly soluble terephthalates of them, and then a carbonate such as sodium carbonate is added to the filtrate obtained, whereby cobalt and manganese are recovered as the forms of the carbonates.

Such conventional methods as described above may be effective for recovering the heavy metal catalyst such as cobalt and manganese without being contaminated with organic impurities and heavy metal impurities which are harmful to the oxidation reaction, but these methods have such troubles in industrial operation that those conventional methods require the complicated procedure of adjusting the pH of the solution and that since the precipitates of the carbonates of the heavy metals formed by such methods are generally obtained as fine particles, it takes a long period of time to recover the precipitates by filtration. Also, the components of the oxidation catalyst effectively recovered by such conventional methods are only the heavy metal components such as cobalt and menganese. Further a method wherein bromine which is other component of the oxidation catalyst can be effectively recovered together with the heavy metal components has not yet been discovered.

SUMMARY OF THE INVENTION

As the results of intense investigations of discovering a method of recovering in high pure states the heavy metals such as cobalt, manganese, etc., and bromine which are the catalyst components from the reaction mother liquor residue of a liquid-phase oxidation reaction, it has now been discovered that heavy metals such as cobalt, manganese, etc., and bromine which are catalyst components can be recovered together in quite high pure states without being contaminated with harmful impurities from the reaction mother liquor residue of the liquid-phase oxidation reaction by stirring the residue with water in the presence of an oxygen-containing gas and a sulfur compound to form an aqueous extract of the catalyst components, whereby the aqueous extract of the catalyst from which the organic impurities and heavy metal impurities as described above been removed is obtained, passing the aqueous extract thus obtained through a column packed with a strongly acidic cation-exchange resin to adsorb thereon the heavy metal catalyst, distilling the aqueous solution passed through the ion-exchange resin column to recover bromine contained in the aqueous solution as hydrobromic acid, and then passing hydrobromic acid through the ion-exchange resin column having adsorbed thereon the heavy metal catalyst to desorb the heavy metal catalyst and recover as the bromides of the heavy metals.

An object of this invention is, therefore, to provide an economical and simple method of recovering in high-pure states the heavy metals such as cobalt, manganese, etc., and bromine which were used as the oxidation catalyst for producing terephthalic acid by the liquid-phase oxidation of an alkylbenzene such as p-xylene in the presence of a lower aliphatic carboxylic acid solvent.

Other object of this invention is to provide a method of recovering the oxidation catalyst components in high purity without being contaminated with organic impurities and metallic impurities such as iron, chromium, molybdenum, lead, copper, tungsten, nickel, etc., which have entered the reaction liquid due to the corrosion of the materials constituting the reaction apparatus and conduits.

Still another object of this invention is to provide a method of recovering economically and easily the heavy metals such as cobalt, manganese, etc., and bromine together in pure states from the aqueous extract of the catalyst components contained in the mother liquor residue of the liquid-phase oxidation reaction by utilizing a strongly acidic cation-exchange resin without need of such complicated operation as the pH adjustment.

Those and other objects of this invention will become apparent from the following descriptions and the accompanying drawings.

BRIEF DESCRIPTION OF THE ACCOMPANYING DRAWINGS

FIG. 1 is a flow sheet showing an embodiment of the method of this invention and FIG. 2 is a graph showing the states that each of such components as cobalt, copper, and sodium leak into the ion-exchanged solution passed through a column packed with a strongly acidic cation-exchange resin when an aqueous extract of catalyst having a cobalt content of 3.0% and an aqueous extract of catalyst having a cobalt content of 0.5% are passed through the ion-exchange resin column.

DETAILED DESCRIPTION OF THE INVENTION

Figure 1:
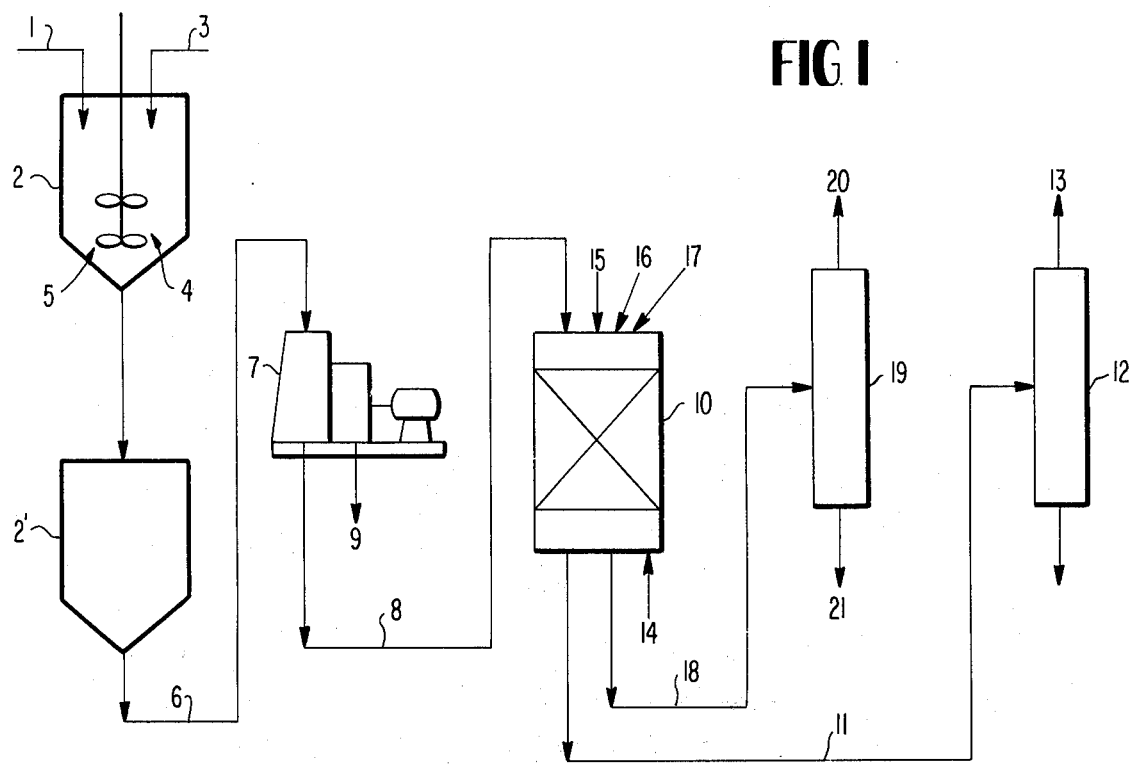

According to the present invention there is provided a method of recovering heavy metals and bromine which are the components of a heavy metal-bromine oxidation catalyst in highly pure states without being contaminated with organic impurities and heavy metal impurities harmful to the oxidation reaction from a reaction mother liquor residue containing the oxidation catalyst, the organic impurities comprising by-products and intermediates of the oxidation reaction, and a small amount of heavy metal impurities, said reaction mother liquor residue having been obtained by separating terephthalic acid from the oxidation reaction product produced by the liquid-phase oxidation of an alkylbenzene such as p-xylene in the presence of the oxidation catalyst using a lower aliphatic mono-carboxylic acid as solvent and then recovering the solvent from the reaction mother liquor by distillation, etc., which method comprises A. stirring said reaction mother liquor residue together with water as solvent by the addition of a sulfur compound selected from the group consisting of hydrogen sulfide, sodium sulfide, sodium hydrosulfide, potassium hydrosulfide, and ammonium hydrosulfide while blowing or pressing in the residue a molecular oxygen-containing gas, whereby the oxidation catalyst is extracted with water, B. subjecting the extracted mixtures thus obtained to a solid-liquid separation to separate impurities as solid materials, C. passing the catalyst-containing extract through a column packed with a strongly acidic cation-exchange resin to adsorb thereon the catalyst heavy metals, D. distilling the ion-exchanged solution passed through the cation-exchange resin-packed column, the solution being the fractions having discharged from the bottom of the column by the time when the catalyst heavy metals just begin to leak in the solution, whereby bromine contained in the solution is recovered as hydrobromic acid, E. passing hydrobromic acid through the column packed with the cation-exchange resin having adsorbed thereon the catalyst heavy metals to desorb the heavy metals, and F. distilling the eluate thus obtained to recover excessive hydrobromic acid and then the bromides of the catalyst heavy metals.

Since the reaction mother liquor residue is extracted by water as solvent in aforesaid steps (A) and (B), the greater part of a large amount of sparingly water-soluble organic impurities contained in the residue are separated from the extracted liquid phase as precipitates or floats. Also, a part of a small amount of the organic impurities remaining dissolved in the extracted liquid-phase are oxidized or polymerized by molecular oxygen contained in the gas blown or pressed in the system in the extraction step and separated from the extracted liquid-phase as precipitates or floats. Furthermore, the heavy metal impurities such as iron and chromium dissolved in the extracted liquid-phase are also oxidized by molecular oxygen in the gas and separated as the precipitates of the oxides. Other heavy metal impurities such as lead, molybdenum, tungsten, copper, nickel, and cadmium react with the sulfur compound added in the extraction step and the precipitates of the sulfides thereof thus formed are separated. Thus, by removing the precipitates or floated matters formed in the extraction step from the extract mixtures by means of a solid-liquid separation, the catalyst extract from which the heavy metal impurities and the greater part of the organic impurities have been removed can be obtained.

Aforesaid steps (A) and (B) in the method of this invention that is, the extraction steps of removing the organic impurities and the heavy metal impurities have the following merits as compared with the conventional methods as disclosed in U.S. Pat. No. 2,964,559 and Japanese Pat. Application Laid Open No. 34,088/'72 as indicated above.

First of all, in the conventional methods as described above, it is required for removing heavy metal impurities such as iron, etc., in the extract mixtures obtained by extracting the reaction mother liquor residue with water to adjust the pH of the extract mixtures above a specific value by adding thereto an alkali. But such a complicated and uneconomical step of pH adjustment is unnecessary in the method of this invention since the heavy metal impurities are removed by the oxygen-containing gas and sulfur compound as stated above. Also, in the case of increasing the pH of the extract mixture above a specific value by the addition of an alkali thereto for separating the heavy metal impurities in the conventional methods as described above, the solubility of the organic impurities in the extract increases according to the increase of the pH value of the extract. Therefore, in order to prevent the organic impurities from being dissolved in the extract in large amount, it has been required in the conventional methods to remove first the insoluble organic impurities from the extract mixtures of the reaction mother liquor residue by solid-liquid separation prior to the step of adjusting the pH value of the extract mixtures. On the other hand, in the method of this invention it is unnecessary to adjust the pH of the extracted mixtures in the steps of removing the heavy metal impurities as described above, hence the method of this invention is not accompanied with such an undesirable phenomenon as increase of the dissolved amount of the organic impurities caused by the increase of the pH value of the extract mixtures as ecountered in the conventional methods. In addition, in the liquid-phase oxidation reaction apparatus for producing terephthalic acid, it is sometimes required for removing the crystals of terephthalic acid attached to the inside wall of the reactor and the filter surface of a centrifugal separator for recovering terephthalic acid from the reaction products and for preventing the occurence of clogging of slurry transporting conduits to wash those equipment with an aqueous solution of sodium hydroxide and hence the pH value of the reaction mother liquor residue is influenced to some extent by the remaining amount of such alkali, but usually the pH value of the residue is about 2.5–3.5. In the method of this invention, therefore, it becomes unnecessary to remove preliminarily the insoluble organic impurities prior to the step of removing the heavy metal impurities from the extract mixtures of the reaction mother liquor residue, and hence by the method of this invention the organic impurities and the heavy metal impurities can be removed simultaneously in one step, which contributes to simplify the operation.

The aqueous extract of the catalyst which was obtained by extracting with water the reaction mother liquor residue in the presence of a molecular oxygen-containing gas and the sulfur compound and from which the organic impurities and the heavy metal impurities have been removed by solid-liquid separation step is then subjected to the subsequent steps of removing completely a small amount of the organic impurities remaining dissolved yet in the aqueous extract and recovering the catalyst components from the extract. That is, the aqueous extract of the catalyst is passed through a column packed with a strongly acidic cation-exchange resin, whereby cobalt and manganese which are the heavy metal components of the catalyst in the extract are selectively adsorbed on the cation-exchange resin. On the other hand, the ion-exchanged solution withdrawn from the bottom of the ion-exchange column passing through the ion-exchange resin layer in the column is collected until leaking of the catalyst heavy metals into the withdrawn solution begins and is distilled for recovering bromine contained therein as hydrobromic acid. If necessary, water may be introduced countercurrently to the column packed with the cation-exchange resin having adsorbed thereon the heavy metals from the bottom, whereby terephthalic acid and such by-products as p-toluic acid and benzoic acid attached to the cation-exchange resin are withdrawn from the top of the column. Furthermore, if necessary, a lower aliphatic carboxylic acid such as acetic acid is passed through the ion-exchange column to remove completely the organic impurities remaining in the ion-exchange resin column. Moreover, if sodium is present in the extract of the catalyst and is adsorbed on the cation-exchange resin as the result of passing the extract through the resin layer, a diluted aqueous solution of a mineral acid such as hydrochloric acid, nitric acid, sulfuric acid, etc., is passed through the ion-exchange resin column to remove the sodium.

Then, by passing hydrobromic acid as eluant through the column of the cation-exchange resin thus treated, cobalt and manganese adsorbed on the cation-exchange resin are desorbed, dissolved in the desorbed solution (this solution is called "eluate" hereafter) as cobalt bromide and manganese bromide, and withdrawn from the column. The eluate thus recovered is distilled to recover first excessive hydrobromic acid after distilling off water therefrom, and finally cobalt bromide and manganese bromide are recovered.

As described above, by the method of this invention cobalt, manganese, and bromine can be recovered in quite highly pure states from the reaction mother liquor residue without being contaminated with the organic impurities and heavy metal impurites which are harmful to the oxidation reaction.

Now, the concentration of the heavy metal catalyst in the aqueous extract of the oxidation catalyst obtained in steps (A) and (B) of this invention as mentioned above depends upon the amount of the oxidation catalyst and the amount of water used as the solvent for the extraction, and thus cannot be defined specifically. But the concentration of cobalt which is the main component of the heavy metal components of the catalyst in the aqueous extract is more than 1%, usually 2–3% or more. In the method of this invention the aqueous extract having such a content of heavy metal may be passed as it is through the cation-exchange resin column. But as the results of the further detailed investigations, we have also discovered the following interesting fact.

That is, when the aqueous extract having a cobalt content of higher than 1% and containing further sodium and such heavy metal impurities as molybdenum, copper, and lead is passed through an cation-exchange resin-packed column, cobalt begins to leak in the eluate passed through the column simultaneously when sodium and the heavy metal impurities begin to leak in the eluate emerging from the column and thus it is difficult, in such case, to remove selectively only sodium and the heavy metal impurities without the loss of cobalt. Therefore, as indicated before, it is required in this invention to remove such impurities as molybdenum, copper, and lead by adding the sulfur compound in steps (A) and (B) and further to pass, when sodium has been adsorbed on the cation-exchange resin, a diluted aqueous solution of a mineral acid through the cation-exchange resin column to dissolve and remove the sodium. However, it has been discovered that when the aqueous extract of the oxidation catalyst is diluted with water so that the concentration of cobalt becomes less than 1.0%, preferably about 0.5% before passing it through the cation-exchange resin column, sodium and such heavy metal impurities as molybdenum, copper, and cobalt, even if they are in the aqueous extract, are selectively carried away through the cation-exchange resin column without adsorption before cobalt begins to leak in the eluate and thus it is possible in such case to adsorb selectively only the heavy metal catalyst components on the ion-exchange resin without adsorbing those impurities on the resin. Therefore, when the aqueous extract of catalyst having a cobalt concentration of lower than 1.0% is obtained or when the aqueous extract of catalyst, even if the concentration of cobalt is higher than 1.0%, is diluted so that the cobalt concentration becomes less than 1.0%, sodium and heavy metal impurities such as molybdenum, copper, and lead can be selectively carried away by the aqueous extract passed through a column packed with an cation-exchange resin, and the aimed heavy metal catalyst only can be selectively adsorbed on the cation-exchange resin by passing the aqueous extract originally having the low cobalt content or the diluted aqueous extract through the cation-exchange resin column. Hence in such case, the addition of the sulfur compound in extraction step (A) described above and the operation of passing a diluted aqueous solution of a mineral acid through the cation-exchange resin-packed column for removing sodium therefrom becomes unnecessary. The present invention further includes such a modification of the recovery system as described above.

By the term "the reaction mother liquor residue" in the oxidation reaction, to which the method of this invention is applied, is meant the tarry or solid residue obtained by distilling off the reaction solvent from the reaction mother liquor formed after recovering terephthalic acid from the reaction product in the production of terephthalic acid by the liquid-phase oxidation of an alkylbenzene such as p-xylene, etc., with a molecular oxygen-containing gas in the presence of a cobalt-bromine or cobalt-manganese-bromine catalyst using a lower aliphatic monocarboxylic acid such as acetic acid, etc., as the reaction solvent. Therefore, any reaction mother liquor residues obtained in the process for producing terephthalic acid by the liquid-phase oxidation of an alkylbenzene in the presence of a heavy metal-halogen catalyst and, if necessary, a reaction initiator such as an aldehyde, a ketone, etc., under any reaction conditions can be employed in the method of this invention regardless of the mode of preparing the residues.

The reaction mother liquor residue thus obtained contains, besides the heavy metal or metals and bromine which are the oxidation catalyst components, the unreacted alkylbenzene, reaction intermediates such as 4-carboxybenzaldehyde and p-toluic acid, by-products having unknown structure, and a small amount of heavy metal impurities such as iron, molybdenum, chromium, tungsten, lead, nickel, copper, etc. which got into the reaction liquor by the corrosion of the materials of the equipment used for the oxidation reaction. But by applying the recovery method of this invention, the heavy metals such as cobalt and manganese and bromine which are the components of the oxidation catalyst used in the reaction can be recovered in good recovery yield and in highly pure states from the reaction mother liquor residue.

Then, the method of this invention will further be explained more in detail by the embodiment illustrated in FIG. 1 of the accompanying drawings.

As shown in the flow sheet of FIG. 1, a concentrated residue obtained by recovering terephthalic acid from the oxidation reaction product withdrawn from the reactor for the liquid-phase oxidation reaction of producing terephthalic acid as described above and then recovering further the reaction solvent by distillation, etc., is charged through a conduit 1 in an extraction chamber 2 equipped with a stirrer and, if necessary, a heating means. Then, water is added to the residue in the chamber through a conduit 3 as the extraction solvent, a sulfur compound such as hydrogen sulfide, sodium sulfide, etc., is added thereto through a conduit 4, and further a molecular oxygen-containing gas is introduced into the reaction system through a conduit 5. The resultant mixture is stirred for a definite period of time at a definite temperature. In the embodiment as illustrated in the figure the extraction procedure is conducted in a single chamber. But, if necessary, the extraction procedure may be practiced in two chambers. In this case, the residue is mixed with water in the first chamber and the mixture of the residue and water is treated with the sulfur compound and the molecular oxygen-containing gas in the second chamber. However, if the cobalt content of the aqueous extract of the catalyst to be passed through an cation-exchange resin-containing column is lower than 1.0%, the addition of the sulfur compound in the aforesaid chamber may be omitted or is unnecessary as will be described later.

After stirring the mixture for a definite period of time, the extract mixtures thus obtained is cooled to a definite temperature in the chamber 2 or in a crystallization chamber 2' and then introduced in a solid-liquid separator 7 through a conduit 6, wherein the extract of catalyst thus separated from solid materials is recovered therefrom through a conduit 8. On the other hand, the separated residue formed in the separator is withdrawn through a conduit 9 and introduced into a proper step of utilizing the organic materials such as intermediates of the oxidation reaction. Further it is necessary that the separated residue is washed with water in the chamber 7 before it is withdrawn therefrom, and the washing water is mixed with the catalyst extract for being treated in the subsequent step, or the washing water be used as the solvent for the extraction step again in the chamber 2 for increasing the recovery yield of the catalyst. The catalyst-containing extract recovered through the conduit 8 is passed through a column 10 packed with a strongly acidic cation-exchange resin as it is or after diluting it with water to adjust the cobalt content to a definite value. The solution thus subjected to the ion-exchange treatment and passed through the column 10 is introduced into a distillation column 12 through a conduit 11, from which bromine in the ion-exchanged solution is recovered through a conduit 13 as hydrobromic acid. After passing the catalyst-containing extract through the ion-exchange resin column, water is introduced, if necessary, from the bottom of the column 10 through a conduit 14 to countercurrently wash the ion-exchange resin packed in the column and, then, if necessary, a lower aliphatic carboxylic acid is passed through the column 10 through a conduit 15. Furthermore, when sodium is adsorbed on the ion-exchange resin, a diluted aqueous solution of a mineral acid is passed through the column through a conduit 16.

Thereafter, hydrobromic acid as eluant is passed through a column 10 of the ion-exchange resin having adsorbed thereon the heavy metal catalyst through a conduit 17 to desorb the heavy metal catalyst. The eluate containing the heavy metal catalyst thus desorbed is withdrawn through a conduit 18 and introduced into a distillation column 19, wherein water is first distilled off, excessive hydrobromic acid, is, then, distilled and recovered through a conduit 20, and finally the heavy metal catalyst is recovered through a conduit 21 as the bromide or bromides thereof.

The aforesaid operation of the method of this invention may be practiced in a continuous system or in a batch system.

Now, each of the operation conditions for conducting the method of this invention will be explained below in detail.

The amount of water to be added into the extraction chamber as a solvent for extracting the oxidation catalyst in the reaction mother liquor residue may be enough necessary for extracting the oxidation catalyst to be recovered therefrom. If the amount of water is excessive, it dissolves unnecessary materials besides the catalyst components, which results in causing the contamination with impurities in the catalyst thus recovered, and further the operation efficiency is reduced greatly due to the increase of the volume of the solution to be treated. On the other hand, if the amount of water is insufficient, the recovery yield of the catalyst is decreased and further the residue to be treated is given an insufficient fluidity, which results in making the stirring operation difficult. In general, the amount of water to be added to the residue is 0.5–6 times by weight, preferably 1–3 times by weight the amount of the residue.

Examples of the sulfur compound to be used for removing a small amount of the heavy metal impurities such as lead, molybdenum, copper, nickel, etc., when they are present in the reaction mother liquor residue include hydrogen sulfide, sodium sulfide, sodium hydrosulfide, potassium hydrosulfide, and ammonium hydrosulfide. Those compounds may be used individually or as mixtures thereof. The amount of the sulfur compound to be added to the residue is one necessary for precipitating the heavy metal impurities such as lead, molybdenum, copper, nickel, etc., in the residue as the sulfides of them. If the sulfur compound is added more than necessary, the catalyst heavy metal or metals are also precipitated as the sulfide or sulfides together with the heavy metal impurities, which results in the reduction of the recovery yield of the catalyst metals. According to our experiments, when cobalt was used as the catalyst metal and the amount of the sulfur in the sulfur compound corresponded to 1% of the total amount of cobalt in the solution to be treated, the loss of cobalt was 1.5%, and when the amount of the sulfur was 0.3% of the total amount of cobalt, the loss of cobalt was 0.5%, that is, the effect of this invention could be sufficiently obtained by the said amount range of the sulfur compound. Therefore, the proper amount of the sulfur compound to be employed is less than 1.0%, preferably less than 0.7%, more preferably less than 0.3% of the amount the catalyst heavy metal as sulfur.

In the case of adding the sulfur compound to the extraction system, it is preferable that the compound is diluted with an inert medium so that the compound is dispersed uniformly as quick as possible. For example, hydrogen sulfide may be diluted with air and other sulfur compound may be diluted with water before the addition thereof to the extraction system.

It is most profitable to utilize air as the molecular oxygen-containing gas to be blown into the extraction system. The amount of the gas may be above the amount of oxygen absorbed in the solution or may be such a volume that the excessive oxygen can be detected while stirring sufficiently the extraction system through which the oxygen-containing gas is blown.

As the operation pressure, that is, the partial pressure of oxygen is higher, the effect of removing the impurities can be obtained in a shorter period of time in the present invention, but the difference in the effect of removing the impurities by the difference in partial pressure of oxygen is quite less. Thus, the preferable range of the operation pressure is from normal pressure to 10 kg./cm$^2$G considering the pressure resistance of reaction vessel.

The temperature of the extraction treatment is preferably from room temperature to 100°C. from the view points of the recovery yield of the catalyst and the ease of operation. If the extraction temperature is lower or higher than the aforesaid temperature range, no particular improvement of the recovery yield of the catalyst and of the purity of the recovered catalyst is obtained.

The extraction period of time depends upon the partial pressure of oxygen and the properties of the reaction mother liquor residue, but is usually longer than 30 minutes.

The extracted mixtures obtained by the above-described process is subjected to a solid-liquid separation by means of an ordinary separator such as a filter, a centrifugal separator, and the like. The solid-liquid separation is preferably conducted at temperatures as low as possible, preferably at temperatures of lower than 50°C. in order to prevent the extract from becoming contaminated with impurities. It is necessary for increasing the recovery yield of the catalyst that the extraction residue thus separated is washed with water and the water used is used as a solvent for the extraction again or is sent to the subsequent step together with the extract thus separated.

The extract thus obtained by the solid-liquid separation or a mixture of the extract and water used for washing the separated residue is passed through a column packed with an cation-exchange resin for adsorbing thereon the catalyst heavy metal or metals. Any strongly-acidic type of cation-exchange resins may be used in the present invention. The amount of the strongly acidic cation-exchange resin to be packed in the column is determined by the equivalent of the catalyst heavy metal or metals and the exchange capacity of the strongly-acidic cation-exchange resin to be used. For example, when the exchange capacity of the strongly-acidic cation-exchange resin is 1.75 meq./ml. and the equivalent of the heavy metal contained in the extract to be processed by the ion-exchange resin is 1.75 eq., the amount of the ion-exchange resin necessary for adsorbing the heavy metal is $$1.75 \times 10^3 \text{ (meg.)} 1.75 \text{ (meq./ml.)} = 10^3 \text{ ml.}$$

It is proper that the passing speed of the extract be 1–10 $(hr.^{-1})$, preferably 5–10 $(hr^{-1})$ in space velocity. The supply of the extract to the ion-exchange resin column is stopped at the point when the catalyst heavy metal or metals begin to leak in the ion-exchanged solution emerging from the bottom of the column.

In addition, when the sulfur compound is not added in the extraction step, that is, when a small amount of molybdenum, copper, lead, etc., are contained in the extract as impurities and the concentration of cobalt in the extract is over 1%, it is necessary to dilute the extract with water so that the concentration of cobalt becomes lower than 1%, preferably about 0.5% as stated before.

Figure 2:
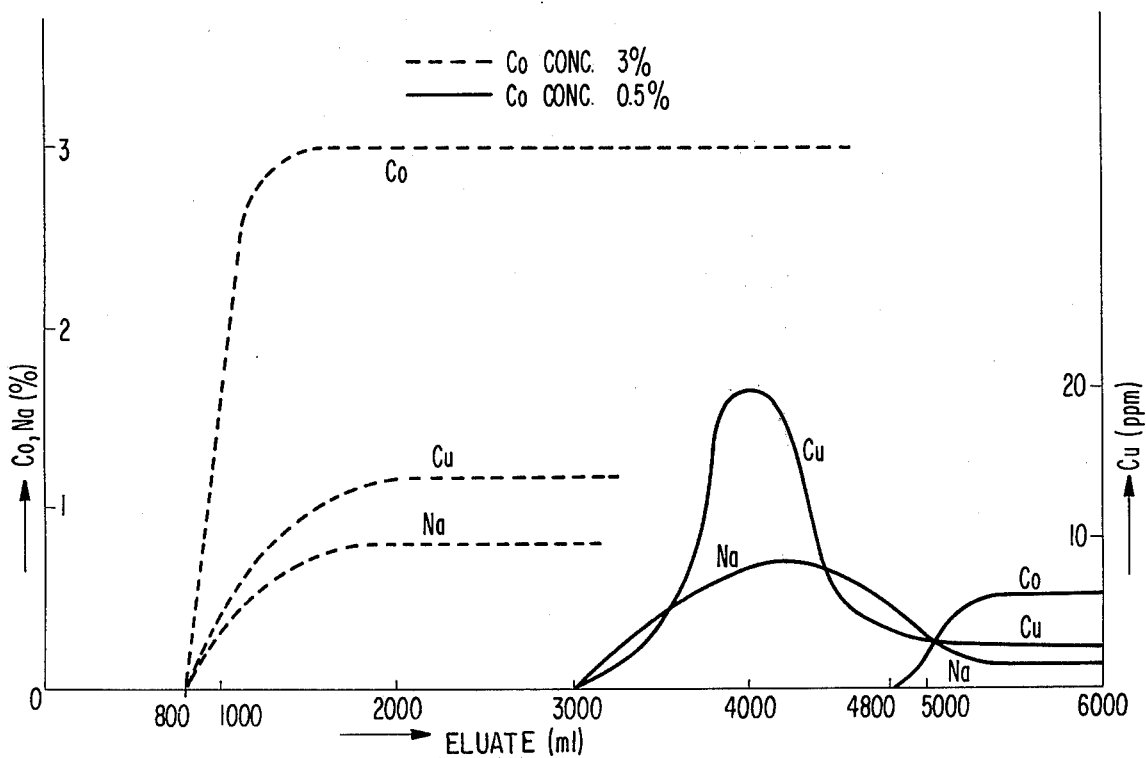

FIG. 2 of the accompanying drawings is a graph showing the state of cobalt, copper, and sodium appearing in the ion-exchanged solution emerging from the bottom of a column (diameter 2.5 cm.) packed with 490 ml. of a strongly-acidic cation-exchange resin, Diaion PK-216 (trade name, made by Mitsubishi Chemical Industries Co., Ltd. exchange capacity 1.75 meq./ml.) in a height of 100 cm. when an aqueous extract of catalyst (containing 0.78% sodium and 14 ppm. copper as impurities) having a cobalt concentration of 3.0% and a solution prepared by diluting the aqueous extract of catalyst with water having a cobalt concentration of 0.5% (0.13% sodium and 2.4 ppm. copper) are passed through the ion-exchange resin column at a space velocity of 5 $hr.^{-1}$. From the results shown in the graph it will be understood that when the diluted aqueous extract of catalyst is passed through the ion-exchange resin column, the impurities such as copper, sodium, etc., can be separated efficiently from cobalt.

By distilling the ion-exchanged solution thus withdrawn from the ion-exchange resin column (the fractions until the catalyst heavy metal just begins to leak in the solution) in a distillation column, water is first distilled off and then a fraction enriched with hydrobromic acid is distilled. Thus, hydrobromic acid can be recovered in high concentration by the distillation procedure.

On the other hand, after the supply of the extract to the ion-exchange resin column is stopped, water displacement is conducted for completely displacing the extract remaining in the ion-exchange resin column with water by passing water through the column at a space velocity of 5–10 $hr.^{-1}$. The amount of the displacement water is about ½ of the amount of the ion-exchange resin packed in the column. It is preferable to use the water used for the displacement as the solvent for extraction.

After water displacement, water is passed through the ion-exchange resin column from the bottom of it to countercurrently wash the resin, whereby benzoic acid and other organic impurities which have been attached to the upper portion of the ion-exchange resin packed in the column are withdrawn from the top of the column. The countercurrent washing with water is ordinarily conducted for about 5–30 minutes at a line velocity of 10–20 meters/hr.

After countercurrent washing with water, a lower aliphatic carboxylic acid is, if necessary, passed through the ion-exchange resin column to remove the organic impurities remaining in the column. Examples of such a low aliphatic carboxylic acid are acetic acid, propionic acid, and butyric acid, and acetic acid is mainly used for the purpose. Such an acid is used as the aqueous solution thereof and when, for example, aqueous 10% acetic acid solution is employed, it is proper that the solution in an amount of less than 5 times the amount of the ion-exchange resin packed in the column is passed through the column at a space velocity of 5–10 $hr.^{-1}$ Also, when the extract of catalyst containing sodium is passed through a cation-exchange resin column with a cobalt concentration of higher than 1.0%, sodium is also adsorbed on the cation-exchange resin together with cobalt and manganese, and thus it is required to remove the sodium from the ion-exchange resin. The removal of sodium is accomplished by passing a diluted aqueous solution of a mineral acid such as hydrochloric acid, nitric acid, sulfuric acid, etc., through the ion-exchange resin column. The proper concentration of the aqueous mineral acid solution is 0.005–0.05 normal, preferably 0.01–0.03 normal. If the concentration of the mineral acid is higher, the amount of the solution to be passed through the ion-exchange resin column may be less, but the amount of the catalyst heavy metal carried away by the acid solution becomes larger, which reduces the recovery yield of the catalyst. On the other hand, if the concentration of the mineral acid is lower, the amount of the catalyst heavy metal carried away by the solution may be reduced but the amount of the solution required for the treatment becomes larger, which results in prolonging the treatment period of time. The amount of the acid solution to be passed through the ion-exchange resin column depends on the amount of sodium to be removed, and it is proper that 0.01–0.03 normal solution of the mineral acid is passed through the column at a space velocity of 5–10 $hr.^{-1}$ Then, the catalyst heavy metal or metals adsorbed on the cation-exchange resin are desorbed by hydrobromic acid and in this case it is proper to pass 3–4 normal solution of hydrobromic acid through the ion-exchange resin column at a line velocity of 1–10, the amount of hydrobromic acid being more than 2 times by equivalent the amount of the catalyst heavy metal or metals. That is, whether the concentration of hydrobromic acid is higher or lower than 3–4 normals, the desorption of the catalyst heavy metal is not influenced substantially, but if the concentration is higher than 3–4 normals, the ion-exchange resin is damaged greatly, and if the concentration is lower than 3–4 normals, the amount of the solution required for desorbing the heavy metal is increased, both cases being undesirable. Also, if the amount of hydrobromic acid contained in the aqueous solution is less than 2 times by equivalent the amount of the catalyst heavy metal to be desorbed, the desorption rate is reduced and thus it is necessary for desorbing completely the catalyst heavy metal from the ion-exchange resin to use the aqueous solution in an amount of higher than 2 times by equivalent.

The eluate containing the desorbed heavy metal catalyst and the excess hydrobromic acid thus obtained from the ion-exchange resin column is sent to a distillation column wherein the excessive hydrobromic acid is first recovered and then the catalyst heavy metal is recovered as the bromide thereof.

As explained in detail, by the method of this invention the catalyst heavy metals such as cobalt and manganese can be recovered from the reaction mother liquor residue with a recovery yield of higher than 85% without being contaminated with harmful impurities and further bromine, the recovery of which has been difficult in conventional methods, can be also recovered with good recovery yield together with cobalt and manganese. Therefore, the method of this invention is quite excellent industrially as well as economically. In particular, by the method of this invention the catalyst components can be recovered in quite pure states without containing harmful impurities and hence if the method of this invention is applied to the recovery of the catalyst used in the production of high-purity terephthalic acid, high-purity terephthalic acid can be produced economically by repeatedly using the recovered catalyst as it is, which makes the present invention more profitable.

Then, the invention will be illustrated in and by the following examples more practically.

EXAMPLE 1

I. Terephthalic acid was prepared by subjecting p-xylene to a liquid-phase air oxidation using acetic acid as the reaction solvent and using cobalt bromide, manganese acetate, and hydrobromic acid (the content of manganese being 5.0% by weight of the amount of cobalt and the content of bromine atom being 3.0 times the content of cobalt) as the catalyst and the reaction mother liquor obtained by separating terephthalic acid formed from the reaction product was introduced into a distillation column, wherein acetic acid was recovered. On the other hand, the tarry residue containing a large amount of the oxidation catalyst was withdrawn from the bottom of the distillation column.

The bottom fraction thus recovered was, then, introduced into a concentration column (316 L made) equipped with a stirrer, a reflux condenser and heater, and the fraction was concentrated for 45 minutes at 160°C. and 600 mm. Hg to separate completely the volatile matters such as acetic acid, etc., whereby the reaction mother liquor residue was obtained. The catalyst components in the residue are shown in the following table together with the contents of heavy metal impurities.

Table 1

| Component | Co | Mn | Fe | Cr | Cu | Mo | Pb | Br |
|---|---|---|---|---|---|---|---|---|
| Conent | 4.6% | 0.23% | 0.32% | 0.09% | 12ppm | 6ppm | 4ppm | 4.5% |

II. In the aforesaid concentration column was remained 700 kg. of the reaction mother liquor residue and after adding thereto 1050 kg. of water, the mixture was maintained at 70°C. Then, the mixture was stirred for 2 hours by blowing 300 liters/min. of air into the mixture together with 40 liters (at normal pressure) of a hydrogen sulfide gas. Thereafter, the residue-water mixture thus treated was introduced in a crystallization chamber, wherein it was cooled to 30°C., and then the mixture was subjected to solid-liquid separation by means of a centrifugal separator to provide about 950 kg. of a filtrate (extract).

The contents of the catalyst components and the impurities in the extract are as shown in Table 2. The extraction percentage of cobalt from the residue was 89% and the solid extraction-residue was washed with water and the water was used as the solvent for the extraction again.

Table 2

| Component | Co | Mn | Fe | Cr | Cu | Mo | Pb | Br |
|---|---|---|---|---|---|---|---|---|
| Content | 3.0% | 0.15% | 59ppm | 5.4ppm | 1.5ppm | 0.7ppm | 0.5ppm | 3.0% |

III. Then, 500 kg. of the extract obtained by the above-described procedure was passed through a column packed with 300 liters of a strongly-acidic cation-exchange resin having an exchange capacity of 1.75 meq./ml. in a height of 100 cm. at a space velocity of 5 hr.$^{-1}$ to adsorb cobalt and manganese on the ion-exchange resin (the amount of cobalt adsorbed was about 15 kg. and the amount of manganese adsorbed was 0.7 kg.). The supply of the extract was stopped when cobalt began to leak in the solution discharged from the bottom of the column (detected by the change of pH). Then, 300 liters of water was passed through the ion-exchange resin column at a space velocity of 10 hr.$^{-1}$ to displace the extract remaining in the column by water. The water used for the displacement was further used as the solvent for the next extraction of catalyst. Thereafter, the ion-exchange resin column was countercurrently washed with water at a line velocity of 10 meters/hr. for 20 minutes and then 300 liters of 10% acetic acid solution was passed through the ion-exchange resin column at a space velocity of 10 hr.$^{-1}$ to remove completely the organic impurities remaining the column. Then, 400 liters of 3 normal solution of hydrobromic acid was passed through the column of the ion-exchange resin having adsorbed the catalyst heavy metals at a line velocity of 3 meters/hr., whereby cobalt and manganese were desorbed.

The eluate containing cobalt and manganese desorbed as the form of bromide and excessive hydrobromic acid was distilled to remove first water, then, 50 kg. of excessive hydrobromic acid, and finally 61 kg. of a solid product consisting of cobalt and manganese were recovered.

The contents of the catalyst components and the heavy metal impurities in the solid product are shown in Table 3. The recovery rate the cobalt from the extract was 97%.

Table 3

| Component | Co | Mn | Fe | Cr | Cu | Mo | Pb | Br |
|---|---|---|---|---|---|---|---|---|
| Content | 23.8% | 1.2% | 0.04% | 0.004% | <3ppm | <3ppm | <3ppm | 74.6% |

On the other hand, by distilling about 350 kg. of the ion-exchanged solution obtained by passing the aforesaid extract through the cation-exchange resin column, about 15 kg. of hydrobromic acid was obtained.

IV. In a small amount of water were dissolved 26.8 kg. of cobalt bromide, 1.4 kg. of manganese bromide, and 2.1 kg. of hydrobromic acid (47% aqueous solution) recovered by the aforesaid procedure and then the solution thus prepared was fed in a 20 liter pressure reactor having titianium lining together with 6 tons of 97% acetic acid. Then after heating the mixture to 190°C. at a pressure of 17 kg./cm.$^2$, p-xylene was introduced into the mixture at a rate of 1 ton/hr. for 90 minutes while blowing air at a rate of 4.2 m$^3$ per kg. of p-xylene. After the reaction was over, the reaction product was introduced in a crystallization chamber to ripen the crystal of terephthalic acid and then the product was subjected to centrifugal separation to separate solid terephthalic acid, which was washed sufficiently with acetic and dried to give the product. The properties and yield of the terephthalic acid is shown in Table 4 described below. The quality of the product was so high that it could be used in direct polymerization reaction with glycols.

EXAMPLE 2

The same catalyst recovery procedure as in Example 1-(III) was followed except that the operation of passing 300 liters of 10% acetic acid through the cation-exchange resin column was omitted. The contents of the catalyst components and the heavy metal impurities in the solid thus recovered are same as the results shown in Table 3.

Then, using the catalyst thus recovered, terephthalic acid was produced by the same manner as in Example 1-(IV). The properties and the yield of the terephthalic acid thus produced was shown in Table 4. In this case, owing to the slightly insufficient removal of the organic impurities caused by the omission of the operation of passing an aqueous acetic acid solution through the column of the cation-exchange resin having adsorbed thereon the heavy metal catalyst, color difference b-value was slightly worse than that of the terephthalic acid obtained by the process in Example 1-(IV) but the product had sufficiently high quality for direct polymerization reaction.

COMPARATIVE EXAMPLE 1

The extract of catalyst obtained in Example 1-(II) was concentrated to remove water, and in order to compensate the deficiency of bromine, hydrobromic acid was added to the extract to adjust the contents of cobalt, manganese, and bromine based on the solvent as in Example 1-(IV). Then, terephthalic acid was prepared by the same way as in Example 1-(IV). The properties and the yield of the terephthalic acid thus prepared are shown in Table 4. As shown in the table, color difference b-value of the terephthalic acid was considerably worse owing to a considerable amount of organic impurities in the catalyst solution thus recovered.

Table 4

|  | Example 1 | Example 2 | Comparative Example 1 |
|---|---|---|---|
| Purity (weight%) | 99.97 | 99.97 | 99.97 |
| Content of 4-carboxy-benzaldehyde (ppm) | 200 | 200 | 240 |
| Color difference b-value | −0.3 | −0.15 | 3.5 |
| Yield (weight%) | 96 | 96 | 95 |

(Note):
Color difference b-value is the external color of terephthalic acid (solid) when the reflected light is measured in accordance with XYZ system by means of a color difference meter CM-20 type made by Color Machine K. K. and the b-value shows the extent of from yellow (+) to blue (−). As the value is smaller (the value is larger when the sign is minus), the color is better.

EXAMPLE 3

I. By following the same procedures as in Example 1-(I) and (II) except that the reaction mother liquor residue containing sodium was used as the starting material to be treated and also the blowing of hydrogen sulfide gas in the extraction step was omitted, about 950 kg. of an extract was obtained. The contents of the catalyst components and the impurities in the extract thus obtained are shown in Table 5.

Table 5

| Component | Co | Mn | Fe | Cr | Cu | Mo | Pb | Na | Br |
|---|---|---|---|---|---|---|---|---|---|
| Content | 3.0% | 0.15% | 59ppm | 5.4ppm | 7.2ppm | 3.6ppm | 2.4ppm | 0.48% | 3.0% |

II. The extract (cobalt concentration 3.0%) thus obtained was diluted with water so that the cobalt concentration became 0.5%. Then, 3000 kg. of the diluted extract was passed through a column packed with 300 liters of a strongly-acidic cation-exchange resin having an exchange capacity of 1.75 meq./ml. in a height of 100 cm. at a space velocity of 10 hr.$^{-1}$ to adsorb cobalt and manganese on the ion-exchange resin. In this case, such impurities as copper, molybdenum, and sodium in the extract were selectively withdrawn from the ion-exchange resin column without being caught by the resin. The supply of the diluted extract was stopped when cobalt just began to leak in the ion-exchanged solution emerging from the bottom of the ion-exchange resin column. Then, as in Example 1-(III), 300 liters of water was passed through the ion-exchange resin-packed resin-packed column to conduct water displacement followed by the countercurrent washing with water, then, an aqueous 10% acetic acid solution was passed through the ion-exchange resin column, and finally 400 liters of a 3 normal hydrobromic solution was passed through the column at a line velocity of 3. The eluate thus obtained was distilled to recover about 50 kg. of excessive hydrobromic acid and about 60 kg. of a solid mixture of cobalt bromide and manganese bromide. The contents of the catalyst components and impurities in the solid thus recovered are shown in Table 6. The recovery yield of cobalt from the extract was 95%.

As shown in the results, molybdenum, copper, and lead among the heavy metal impurities were considerably observed in the catalyst recovered since the cobalt content of the diluted extract was over 1.0% defined in this invention.

COMPARATIVE EXAMPLE 3.

By following the same procedures as in Example 1-(I) and (II) except that the same reaction mother liquor residue as used in Example 3 was used as the material to be treated and also the operation of air blowing in the extraction system and of sending a hydrogen sulfide gas therein was omitted, an extract of catalyst was obtained and then the extract was diluted with water so that the content of cobalt became 0.5%.

Table 6

| Component | Co | Mn | Fe | Cr | Cu | Mo | Pb | Na | Br |
|---|---|---|---|---|---|---|---|---|---|
| Content | 23.7% | 1.2% | 0.04% | 0.004% | <3ppm | <3ppm | <3ppm | 0.04% | 74.6% |

On the other hand, by distilling about 2850 kg. of the ion-exchange solution withdrawn from an cation-exchange resin column when the aforesaid diluted extract was passed through the cation-exchange resin column, about 15 kg. of hydrobromic acid was recovered.

EXAMPLE 4

By treating the diluted extract as in the manner of Example 3-(II), about 63 kg. of a solid mixture of catalyst was recovered. The contents of the catalyst components and impurities in the solid mixture are shown in Table 9 and the recovery yield of cobalt was 95%. In this comparative example the removal of iron and chromium was insufficient since the blowing of air was not conducted in the extraction step.

Table 9

| Component | Co | Mn | Fe | Cr | Cu | Mo | Pb | Na | Br |
|---|---|---|---|---|---|---|---|---|---|
| Content | 22.6% | 1.1% | 1.0% | 0.23% | 0.002% | 0.001% | <3ppm | 0.04% | 74.7% |

By following the same procedure as in Example 3 except that the extact of catalyst (cobalt concentration 3.0%) in Example 3-(II) was diluted with water so that the content of cobalt became 1.0%, about 60 kg. of a solid mixture of cobalt bromide and manganese bromide was recovered. The contents of the catalyst components and impurities in the solid mixture are shown in Table 7. The recovery yield of cobalt from the extract was 95%.

While the invention has been described in detail and with reference to specific embodiments thereof, it will be apparent to one skilled in the art that various changes and modifications can be made therein without departing from the spirit and scope thereof.

What is claimed is:

1. A method of recovering one or more heavy metal bromides and hydrobromic acid which are the components of an oxidation catalyst in highly-pure states with- Table 7

| Component | Co | Mn | Fe | Cr | Cu | Mo | Pb | Na | Br |
|---|---|---|---|---|---|---|---|---|---|
| Content | 23.7% | 1.2% | 0.04% | 0.004% | 0.002% | 0.001% | <3ppm | 0.05% | 74.7% |

COMPARATIVE EXAMPLE 2.

By following the same procedures as in Example 3 except that the extract of catalyst (cobalt concentration 3.0%) in Example 3-(II) was diluted with water so that the content of cobalt became 1.5%, about 61 kg. of a solid mixture of the catalyst was recovered. The contents of the catalyst components and impurities in the solid mixture are shown in Table 8 and the recovery yield of cobalt from the extract was 95%.

out being contaminated with organic impurities and heavy metal impurities harmful to the oxidation reaction from the reaction mother liquor residue containing the oxidation catalyst, the organic impurities comprising by-products and intermediates of the oxidation reaction, and a small amount of heavy metal impurities, said reaction mother liquor residue having been obtained by separating terephthalic acid from the oxidation reaction product prepared by the liquid-phase oxidation of an alkylbenzene in the presence of heavy metal bromine oxidation catalyst using a lower ali- Table 8

| Component | Co | Mn | Fe | Cr | Cu | Mo | Pb | Na | Br |
|---|---|---|---|---|---|---|---|---|---|
| Content | 23.4% | 1.2% | 0.04% | 0.004% | 0.005% | 0.003% | 0.002% | 0.11% | 74.7% | phatic monocarboxylic acid as the solvent and then recovering the solvent from the reaction mother liquid, which method comprises A. stirring said reaction mother liquor residue together with water as solvent in the presence of a sulfur compound selected from the group consisting of hydrogen sulfide, sodium sulfide, sodium hydrosulfide, potassium hydrosulfide, and ammonium hydrosulfide which converts heavy metal impurities such as lead, molybdenum, copper and nickel to their respective sulfides while blowing a molecular oxygen-containing gas into said residue water mixture or dissolving a molecular oxygen-containing gas into the residue under pressure, whereby the oxidation catalyst is extracted with water, B. subjecting the extracted mixtures thus obtained to a solid-liquid separation to separate impurities as solid materials, C. passing the catalyst-containing extract through a column packed with a strongly-acidic cation-exchange resin to absorb thereon the catalyst heavy metal or metals, D. distilling the ion-exchanged solution passed through the cation-exchange resin-packed column, said solution being the fractions having discharged from the bottom of the column by the time when said heavy metal catalyst just begins to leak in the ion-exchanged solution, whereby bromine contained in the solution is recovered as hydrobromic acid, E. passing hydrobromic acid through the column packed with the cation-exchange resin having absorbed thereon the catalyst heavy metal or metals to desorb the heavy metal or metals therefrom, and F. distilling the eluate thus recovered to recover excessive hydrobromic acid and then the bromide or bromides of the catalyst heavy metal or metals.

2. The method as claimed in claim 1 wherein the amount of sulfur in said sulfur compound to be used is less than 1.0% of the amount of the catalyst heavy metal or metals.

3. The methods as claimed in claim 1 wherein said sulfur compound is hydrogen sulfide and is supplied to the extraction system as a diluted gas with air.

4. The method as claimed in claim 1 wherein said sulfur compound is selected from sodium sulfide, sodium hydrosulfide, potassium hydrosulfide, and ammonium hydrosulfide and is supplied to the extraction system as an aqueous solution of it.

5. The method as claimd in claim 1 wherein sodium is present in the catalyst-containing extract and a diluted aqueous solution of a mineral acid is passed through the column packed with the cation-exchange resin in order to dissolve off sodium adsorbed thereon after the completion of passing the extract of catalyst through said column.

6. The method as claimed in claim 5 wherein said mineral acid is selected from hydrochloric acid, nitric acid, and sulfuric acid.

7. The method as claimed in claim 5 wherein the concentration of said diluted aqueous solution of the mineral acid is 0.005–0.05 normal.

8. A method for recovering one or more heavy metal bromides and hydrobromic acid which are the components of an oxidation catalyst without being contaminated with organic impurities and heavy metal impurities harmful to the oxidation reaction from the reaction mother liquor residue containing the oxidation catalyst, the organic impurities comprising by-products and intermediates of the oxidation reaction, and a small amount of heavy metal impurities, said reaction mother liquor residue having been obtained by separating terephthalic acid from the oxidation reaction product prepared by the liquid-phase oxidation of an alkylbenzene in the presence of heavy metal-bromine oxidation catalyst using a lower aliphatic monocarboxylic acid as the solvent and then recovering the solvent from the reaction mother liquor, which method comprises A. stirring said residue together with water as solvent while blowing a molecular oxygen-containing gas into said residue water mixture or dissolving a molecular oxygen-containing gas into the residue under pressure, whereby the oxidation catalyst is extracted with water, B. subjecting the extracted mixtures thus obtained to a solid liquid separation to separate impurities as solid materials, C. diluting the extract of catalyst thus obtained with water so that the concentration of said catalyst heavy metal or metals becomes less than 1.0%, D. passing the diluted extract of catalyst through a column packed with a strongly-acidic cation-exchange resin to adsorb the catalyst heavy metal or metals on the resin, E. distilling the ion-exchanged solution passed through the cation-exchange resin-packed column, said solution being the fractions having discharged from the bottom of the column by the time when said metal catalyst just begins to leak in the fraction whereby bromine contained in the solution is recovered by hydrobromic acid, F. passing hydrobromic acid through the column of the cation-exchange resin having adsorbed thereon the catalyst heavy metal or metals to desorb the catalyst heavy metal or metals therefrom, and G. distilling the eluate thus obtained to recover excessive hydrobromic acid and then the bromide or bromides of the catalyst heavy metal or metals.

9. The method as claimd in claim 1 wherein said catalyst heavy metals are cobalt and manganese.

10. The method as claimed in claim 1 wherein said molecular oxygen-containing gas is air.

11. The method as claimed in claim 1 wherein said cation-exchange resin column through which the extract of catalyst has been passed is countercurrently washed by passing water from the bottom of the column to remove the organic impurities attached thereto.

12. The method as claimed in claim 1 wherein an aqueous solution of a lower aliphatic carboxylic acid is passed through the cation-exchange resin column through which the extract of catalyst or a diluted solution of the extract of catalyst has been passed in order to dissolve off the organic impurities remaining therein.

13. The method as claimed in claim 12 wherein said lower aliphatic carboxylic acid is acetic acid.

14. The method as claimed in claim 1 wherein an aqueous solution of hydrobromic acid having a concentration of 3–4 normal is used for desorbing the catalyst heavy metal or metals adsorbed on the cation-exchange resin packed in the column.

15. The method as claimed in claim 8 wherein said catalyst heavy metals are cobalt and manganese.

16. The method as claimed in claim 8 wherein said molecular oxygen-containing gas is air.

17. The method as claimed in claim 8 wherein said cation-exchange resin column through which a diluted solution of the extract of catalyst has been passed is countercurrently washed by passing water from the bottom of the column to remove the organic impurities attached thereto.

18. The method as claimed in claim 9 wherein an aqueous solution of a lower aliphatic carboxylic acid is passed through the cation-exchange resin column through which the extract of catalyst or a diluted solution of the extract of catalyst has been passed in order to dissolve off the organic impurities remaining therein.

19. The method as claimed in claim 8 wherein an aqueous solution of hydrobromic acid having a concentration of 3–4 normal is used for desorbing the catalyst heavy metal or metals adsorbed on the cation-exchange resin packed in the column.

20. The method as claimed in claim 18 wherein said lower aliphatic carboxylic acid is acetic acid.

* * * * *